(12) United States Patent
Dalveren et al.

(10) Patent No.: US 12,429,538 B2
(45) Date of Patent: Sep. 30, 2025

(54) ADJUSTABLE MULTISTAGE COIL FOR FUNCTIONAL IMAGING OF LIMB

(71) Applicant: GE Precision Healthcare LLC, Wauwatosa, WI (US)

(72) Inventors: Taylan Dalveren, North Ridgeville, OH (US); Robert Clinton Rainey, Stow, OH (US); Victor Taracila, Orange Village, OH (US); Fraser John Laing Robb, Aurora, OH (US); Jana Michelle Vincent, Aurora, OH (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 355 days.

(21) Appl. No.: 17/678,328

(22) Filed: Feb. 23, 2022

(65) Prior Publication Data
US 2023/0266414 A1    Aug. 24, 2023

(51) Int. Cl.
A61B 5/00 (2006.01)
A61B 5/055 (2006.01)
G01R 33/34 (2006.01)

(52) U.S. Cl.
CPC ........ *G01R 33/34084* (2013.01); *A61B 5/004* (2013.01); *A61B 5/055* (2013.01)

(58) Field of Classification Search
CPC .............................................. G01R 33/34084
See application file for complete search history.

(56) References Cited

U.S. PATENT DOCUMENTS

| | | | | |
|---|---|---|---|---|
| 6,137,291 A * | 10/2000 | Szumowski | ....... | G01R 33/3415 324/218 |
| 6,438,402 B1 * | 8/2002 | Hasoian | ............... | G01R 33/341 600/410 |
| 2016/0077172 A1 * | 3/2016 | Duensing | ......... | G01R 33/34084 600/422 |
| 2019/0086490 A1 * | 3/2019 | You | ..................... | G01R 33/3415 |
| 2019/0154773 A1 * | 5/2019 | Stack | ................ | G01R 33/34084 |
| 2019/0369176 A1 * | 12/2019 | Dalveren | ......... | G01R 33/34007 |
| 2022/0137163 A1 * | 5/2022 | Klomp | ............. | G01R 33/34007 324/322 |
| 2022/0229132 A1 * | 7/2022 | Cher | ................ | G01R 33/34084 |
| 2022/0349966 A1 * | 11/2022 | Zheng | ............. | G01R 33/34007 |
| 2023/0243904 A1 * | 8/2023 | Taracila | ........... | G01R 33/34084 324/318 |

OTHER PUBLICATIONS

Authors et al. Anonymous; "Adjustable Arm Coil for Functional Imaging", IP.com Prior Art Database Technical Disclosure, 2013; pp. 1-4.

* cited by examiner

*Primary Examiner* — Keith M Raymond
*Assistant Examiner* — Gabriel Victor Popescu
(74) *Attorney, Agent, or Firm* — Fletcher Yoder, P.C.

(57) ABSTRACT

A radio frequency (RF) multistage receiving coil assembly for a magnetic resonance imaging (MRI) system is provided. The RF multistage receiving coil assembly includes a plurality of RF coils, wherein each RF coil of the plurality of RF coils includes a plurality of flexible loops having a malleable conductor. The RF multistage receiving coil also includes a plurality of flexible enclosures, wherein a respective RF coil of the plurality of RF coils is disposed within a respective flexible enclosure of the plurality of flexible enclosures. The RF multistage receiving coil assembly is configured to be adjusted and disposed about an extremity of a subject to enable functional imaging of the extremity with the MRI system.

17 Claims, 14 Drawing Sheets

ADJUSTABLE MULTISTAGE COIL FOR FUNCTIONAL IMAGING OF LIMB

BACKGROUND

The subject matter disclosed herein relates to medical imaging and, more particularly, to functional imaging of tissues or organs utilizing a magnetic resonance imaging (MRI) system.

Non-invasive imaging technologies allow images of the internal structures or features of a patient/object to be obtained without performing an invasive procedure on the patient/object. In particular, such non-invasive imaging technologies rely on various physical principles (such as the differential transmission of X-rays through a target volume, the reflection of acoustic waves within the volume, the paramagnetic properties of different tissues and materials within the volume, the breakdown of targeted radionuclides within the body, and so forth) to acquire data and to construct images or otherwise represent the observed internal features of the patient/object.

During MRI, when a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field B1) which is in the x-y plane and which is near the Larmor frequency, the net aligned moment, or "longitudinal magnetization", $M_z$, may be rotated, or "tipped", into the x-y plane to produce a net transverse magnetic moment, $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradient fields vary according to the particular localization method being used. The resulting set of received nuclear magnetic resonance (NMR) signals are digitized and processed to reconstruct the image using one of many well-known reconstruction techniques.

MRI systems may be utilized for functional imaging. Functional imaging helps in revealing physiological activities of tissues and organs within the body of a patient. Functional imaging provides functional attributes of tissues or organs undergoing MRI. Generally, in MRI systems radiofrequency coils include multiple channels as receivers for parallel imaging. Parallel imaging (PI) techniques improve the image quality. However, there are no conventional techniques known that provide functional imaging of a human limb or extremity (e.g., leg or arm).

A conventional technique for imaging body parts of a patient utilizes extremity coils. Extremity coils enable imaging of a specific region of a patient body. Since extremity coils provide localized imaging, there are optimized types of extremity coils for different body parts of the patient (e.g., knee, elbow, ankle, wrist, etc.). Extremity coils provide sensitive and homogenous imaging. However, the position of the extremity coils is static and does not provide functional imaging.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a radio frequency (RF) multistage receiving coil assembly for an MRI system is provided. The RF multistage receiving coil assembly includes a plurality of RF coils, wherein each RF coil of the plurality of RF coils includes a plurality of flexible loops having a malleable conductor. The RF multistage receiving coil assembly also includes a plurality of flexible enclosures, wherein a respective RF coil of the plurality of RF coils is disposed within a respective flexible enclosure of the plurality of flexible enclosures. The RF multistage receiving coil assembly is configured to be adjusted and disposed about an extremity of a subject to enable functional imaging of the extremity with the MRI system.

In another embodiment, an MRI system is provided. The MRI system includes an RF multistage receiving coil assembly. The RF multistage receiving coil assembly includes a plurality of RF coils, wherein each RF coil of the plurality of RF coils includes a plurality of flexible loops having a malleable conductor. The RF multistage receiving coil assembly also includes a plurality of flexible enclosures, wherein a respective RF coil of the plurality of RF coils is disposed within a respective flexible enclosure of the plurality of flexible enclosures. The RF multistage receiving coil assembly is configured to be adjusted and disposed about an extremity of a subject to enable functional imaging of the extremity with the MRI system.

In a further embodiment, an RF multistage receiving coil assembly for an MRI system is provided. The RF multistage receiving coil assembly includes a plurality of stages, wherein each stage includes an RF coil disposed within a flexible enclosure, and each RF coil includes a plurality of flexible loops having a malleable conductor. The RF multistage receiving coil assembly is configured to be adjusted and disposed about an extremity of a subject to enable functional imaging of the extremity with the MRI system. Each stage of the plurality of stages is configured to be moved with respect to each other along a longitudinal axis of the RF multistage receiving coil assembly. The RF multistage receiving coil assembly is configured to operate in a first mode with only some of the RF coils selectively activated during a MRI scan and in a second mode with all of the RF coils activated during the MRI scan.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

Figure 1:
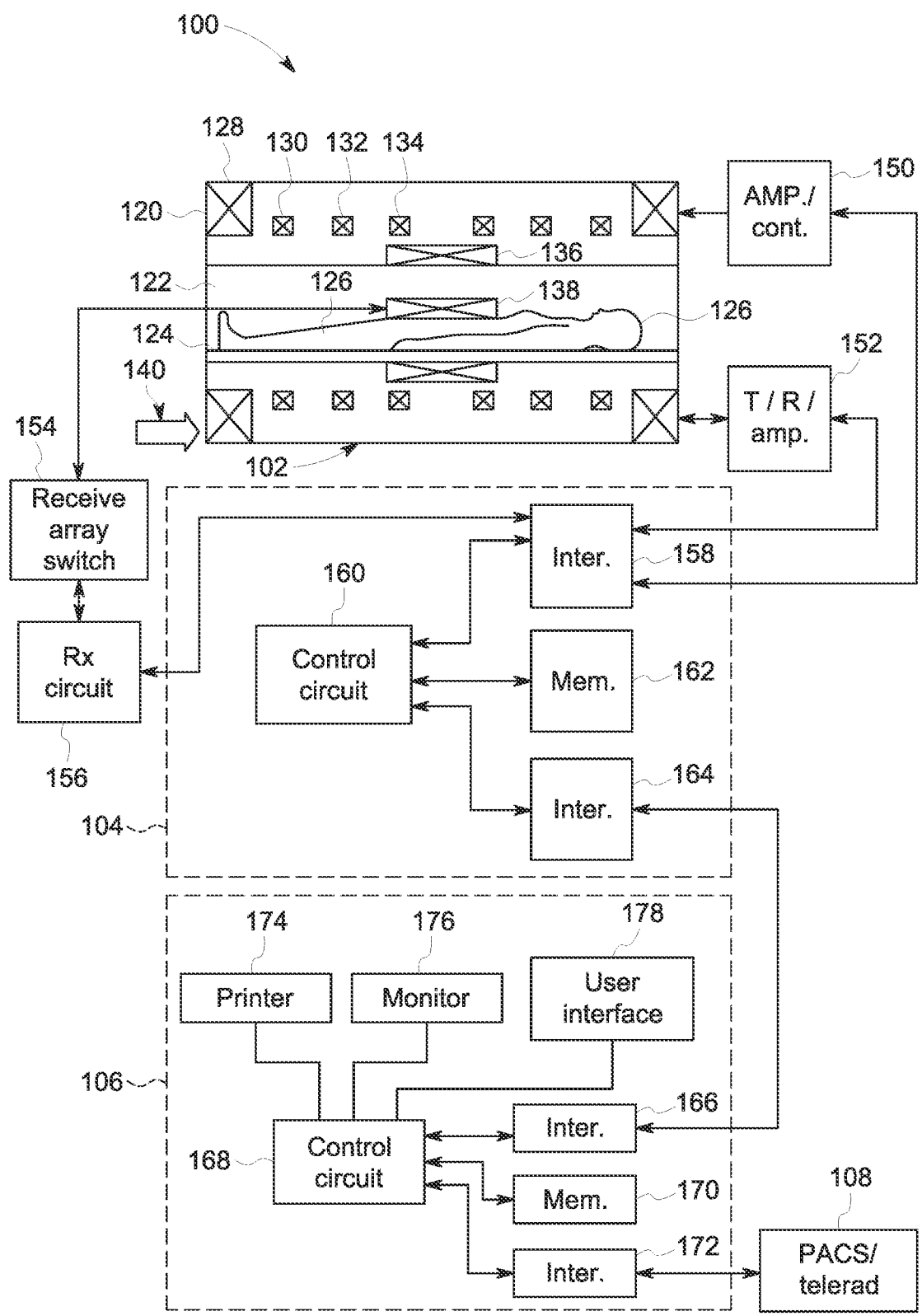
FIG. 1 illustrates an embodiment of a magnetic resonance imaging (MRI) system suitable for use with the disclosed technique.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The disclosed embodiments provide for an RF multistage receiving coil assembly that enables functional imaging (e.g., of functional attributes) of an extremity (e.g., arm or leg). The RF multistage receiving coil assembly includes multiple stages or segments, wherein each segment includes an RF receiving coil disposed within a flexible enclosure. Each RF receiving coil includes multiple flexible loops (e.g., elements or channels) having a malleable conductor. The number of total channels for the RF multistage receiving coil assembly is greater than 32 channels. The RF multistage receiving coil assembly may span an arm from wrist to shoulders or a leg from adjacent the glutes to the ankle. Each stage of the RF multistage receiving coil assembly can be individually adjusted about the extremity. The RF multistage receiving coil enables dynamic imaging of the extremity instead of static imaging. The RF multistage receiving coil enables activities to be performed by a patient to image the muscles in various states of tension. For example, the patient moves their arm or leg to enable imaging the muscles in their relaxed or tensed state. The channels in the RF multistage receiving coil function as a receiver of RF energy of a specific resonance frequency emitted by molecules in the patient body. Due to the high channel count and the flexibility of the loops, the RF multistage receiving coil assembly maximizes acceleration in all directions during parallel imaging to provide efficient capture of movement and related stress of the muscles of the extremity. Functional imaging of an extremity may be quite useful for athletes (e.g., for legs and arms) and musicians (e.g., for arms) who have a higher tendency to injure a muscle in an extremity.

With the preceding in mind, FIG. 1 a magnetic resonance imaging (MRI) system 100 is illustrated schematically as including a scanner 102, scanner control circuitry 104, and system control circuitry 106. According to the embodiments described herein, the MRI system 100 is generally configured to perform MR imaging.

System 100 additionally includes remote access and storage systems or devices such as picture archiving and communication systems (PACS) 108, or other devices such as teleradiology equipment so that data acquired by the system 100 may be accessed on- or off-site. In this way, MR data may be acquired, followed by on- or off-site processing and evaluation. While the MRI system 100 may include any suitable scanner or detector, in the illustrated embodiment, the system 100 includes a full body scanner 102 having a housing 120 through which a bore 122 is formed. A table 124 is moveable into the bore 122 to permit a patient 126 to be positioned therein for imaging selected anatomy within the patient.

Scanner 102 includes a series of associated coils for producing controlled magnetic fields for exciting the gyromagnetic material within the anatomy of the subject being imaged. Specifically, a primary magnet coil 128 is provided for generating a primary magnetic field, B0, which is generally aligned with the bore 122. A series of gradient coils 130, 132, and 134 permit controlled magnetic gradient fields to be generated for positional encoding of certain of the gyromagnetic nuclei within the patient 126 during examination sequences. A radio frequency (RF) coil 136 (e.g., RF transmit coil) is configured to generate radio frequency pulses for exciting the certain gyromagnetic nuclei within the patient. In addition to the coils that may be local to the scanner 102, the system 100 also includes a set of receiving coils or RF receiving coils 138 (e.g., an array of coils) configured for placement proximal (e.g., against) to the patient 126. As an example, the receiving coils 138 can include cervical/thoracic/lumbar (CTL) coils, head coils, single-sided spine coils, and so forth. In certain embodiments, the RF receiving coils 138 may be part of a multi-stage coil disposed about an extremity (e.g., arm or leg) of the patient 126 as described below. Generally, the receiving coils 138 are placed close to or on top of the patient 126 so as to receive the weak RF signals (weak relative to the transmitted pulses generated by the scanner coils) that are generated by certain of the gyromagnetic nuclei within the patient 126 as they return to their relaxed state.

The various coils of system 100 are controlled by external circuitry to generate the desired field and pulses, and to read emissions from the gyromagnetic material in a controlled manner. In the illustrated embodiment, a main power supply 140 provides power to the primary field coil 128 to generate the primary magnetic field, Bo. A power input 44 (e.g., power from a utility or grid), a power distribution unit (PDU), a power supply (PS), and a driver circuit 150 may together provide power to pulse the gradient field coils 130, 132, and 134. The driver circuit 150 may include amplification and control circuitry for supplying current to the coils as defined by digitized pulse sequences output by the scanner control circuit 104.

Another control circuit 152 is provided for regulating operation of the RF coil 136. Circuit 152 includes a switching device for alternating between the active and inactive modes of operation, wherein the RF coil 136 transmits and does not transmit signals, respectively. Circuit 152 also includes amplification circuitry configured to generate the RF pulses. Similarly, the receiving coils 138 are connected to switch 154, which is capable of switching the receiving coils 138 between receiving and non-receiving modes. Thus, the receiving coils 138 resonate with the RF signals produced by relaxing gyromagnetic nuclei from within the patient 126 while in the receiving mode, and they do not resonate with RF energy from the transmitting coils (i.e., coil 136) so as to prevent undesirable operation while in the non-receiving mode. Additionally, a receiving circuit 156 is configured to receive the data detected by the receiving coils 138 and may include one or more multiplexing and/or amplification circuits.

It should be noted that while the scanner 102 and the control/amplification circuitry described above are illustrated as being coupled by a single line, many such lines may be present in an actual instantiation. For example, separate lines may be used for control, data communication, power transmission, and so on. Further, suitable hardware may be disposed along each type of line for the proper handling of the data and current/voltage. Indeed, various filters, digitizers, and processors may be disposed between the scanner and either or both of the scanner and system control circuitry 104, 106.

As illustrated, scanner control circuit 104 includes an interface circuit 158, which outputs signals for driving the gradient field coils and the RF coil and for receiving the data representative of the magnetic resonance signals produced in examination sequences. The interface circuit 158 is coupled to a control and analysis circuit 160. The control and analysis circuit 160 executes the commands for driving the circuit 150 and circuit 152 based on defined protocols selected via system control circuit 106.

Control and analysis circuit 160 also serves to receive the magnetic resonance signals and performs subsequent processing before transmitting the data to system control circuit 106. Scanner control circuit 104 also includes one or more memory circuits 162, which store configuration parameters, pulse sequence descriptions, examination results, and so forth, during operation.

Interface circuit 164 is coupled to the control and analysis circuit 160 for exchanging data between scanner control circuit 104 and system control circuit 106. In certain embodiments, the control and analysis circuit 160, while illustrated as a single unit, may include one or more hardware devices. The system control circuit 106 includes an interface circuit 166, which receives data from the scanner control circuit 104 and transmits data and commands back to the scanner control circuit 104. The control and analysis circuit 168 may include a CPU in a multi-purpose or application specific computer or workstation. Control and analysis circuit 168 is coupled to a memory circuit 170 to store programming code for operation of the MRI system 100 and to store the processed image data for later reconstruction, display and transmission. The programming code may execute one or more algorithms that, when executed by a processor, are configured to perform reconstruction of acquired data as described below. In certain embodiments, the memory circuit 170 may store one or more neural networks for reconstruction of acquired data as described below. In certain embodiments, image reconstruction may occur on a separate computing device having processing circuitry and memory circuitry.

An additional interface circuit 172 may be provided for exchanging image data, configuration parameters, and so forth with external system components such as remote access and storage devices 108. Finally, the system control and analysis circuit 168 may be communicatively coupled to various peripheral devices for facilitating operator interface and for producing hard copies of the reconstructed images. In the illustrated embodiment, these peripherals include a printer 174, a monitor 176, and user interface 178 including devices such as a keyboard, a mouse, a touchscreen (e.g., integrated with the monitor 176), and so forth.

Figure 2:
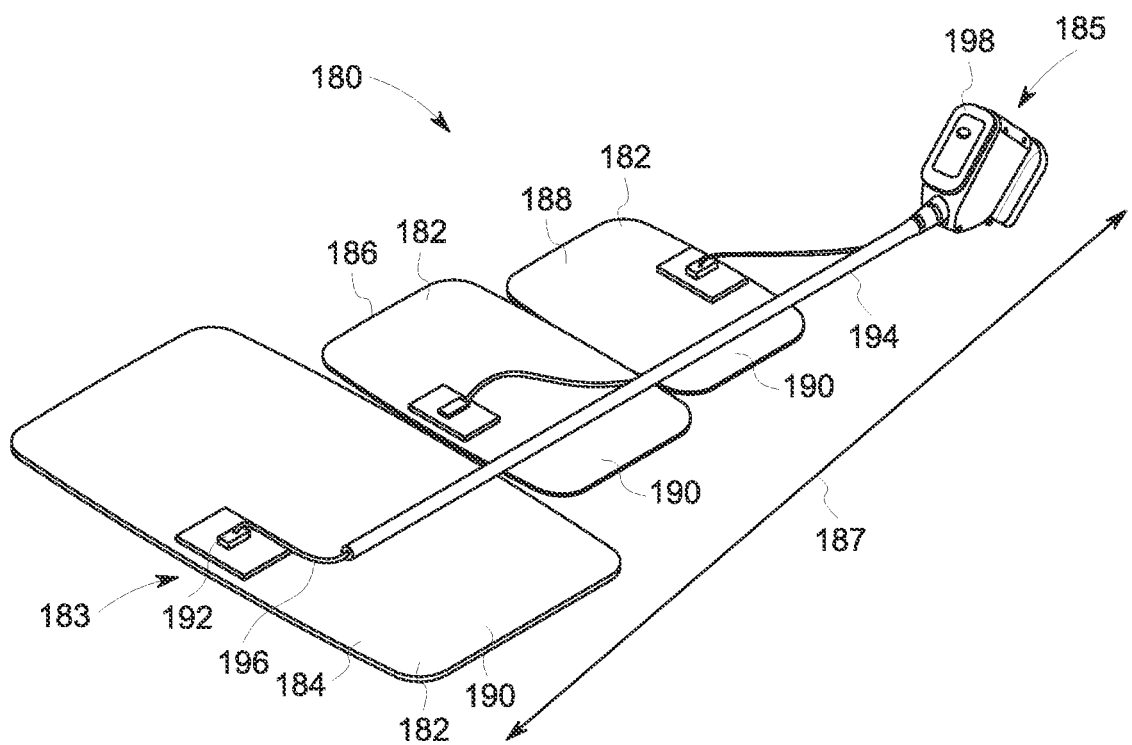
FIG. 2 is a perspective view of an RF multistage receiving coil assembly for functional imaging of an extremity (e.g., with stages in a flat position), in accordance with aspects of the present disclosure.

FIG. 2 is a perspective view of an RF multistage receiving coil assembly 180 for functional imaging of an extremity. The RF multistage receiving coil assembly 180 functions as an RF receiving coil in an MRI system (e.g., RF receiving coil 138 in FIG. 1) to enable functional imaging of an extremity (e.g., arm or leg). The RF multistage receiving coil assembly 180 may operate with a magnetic field strength of 1.5 Tesla (T) or 3.0 T. The RF multistage receiving coil assembly 180 in FIG. 2 is configured for functional imaging of an arm. In particular, the RF multistage receiving coil assembly 180 enables functional imaging between the shoulder and the wrists. The RF multistage receiving coil assembly 180 enables dynamic arm imaging instead of static imaging. In particular, the multistage receiving coil assembly 180 enables activities (e.g., bending, straightening, twisting, clinching, etc.) to be performed by a patient to image the muscles in various states of tension. For example, the patient moves the arm to enable imaging of the muscles in their relaxed or tensed state.

In certain embodiments, the RF multistage receiving coil assembly 180 may be configured for functional imaging of a leg. In particular, the RF multistage receiving coil assembly 180 enables functional imaging between the glutes and the ankle. The shape and sizes of the various stages may vary from those depicted in FIG. 2 to accommodate the shape of the leg.

The RF multistage receiving coil assembly 180 includes multiple stages 182 (e.g., stages 184, 186, and 188). The number of stages 182 may vary (e.g., 2, 3, 4, 5, or more). At minimum, the RF multistage receiving coil assembly 180 includes at least two stages. As depicted, the RF multistage receiving coil assembly 180 includes 3 stages. The shape and size of each stage 182 may vary. As depicted, stage 184 is larger than both stages 186, 188. Stage 186 is larger than stage 188. In other words, the stages 182 decrease in size from one longitudinal end 183 to the other longitudinal end 185 along a longitudinal length 187 of the RF multistage receiving coil assembly 180. In certain embodiments, the stages 182 may increase in size from the longitudinal end 183 to the longitudinal end 185. In certain embodiments, the stage 186 may be the largest stage.

Figure 3:
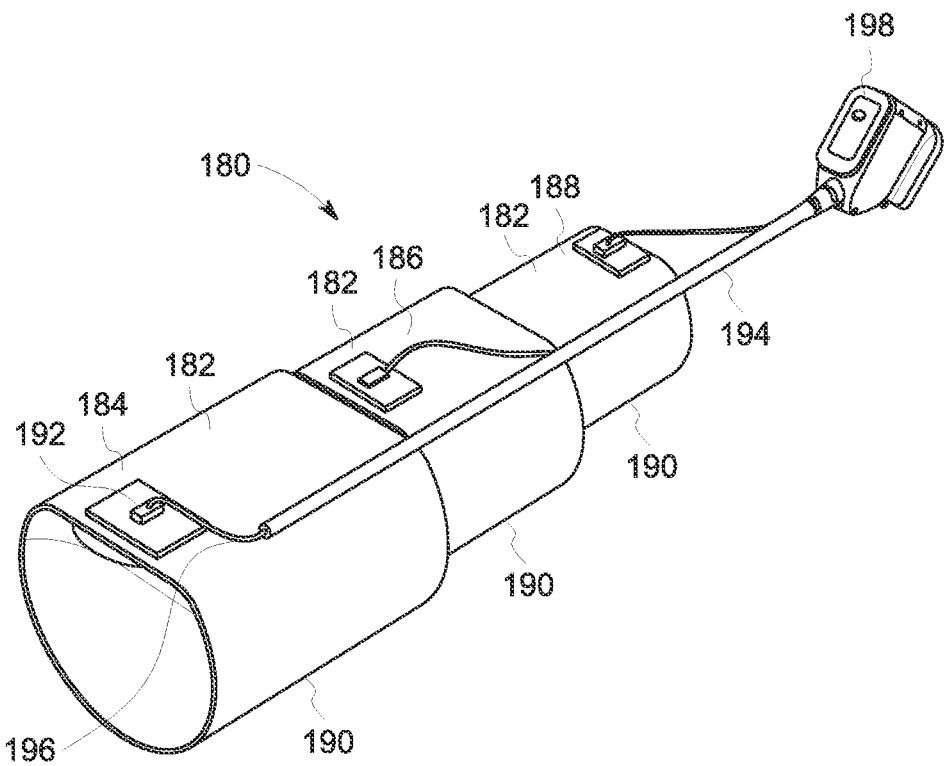
FIG. 3 is a perspective view of an RF multistage receiving coil assembly for functional imaging of an extremity (e.g., with the stages in a flexed position), in accordance with aspects of the present disclosure.

Each stage 182 includes an RF receiving coil (e.g., flexible RF coil) disposed within a flexible enclosure 190 (e.g., blanket, cuff, wrap, etc.). Each RF coil includes multiple flexible loops (e.g., channels or elements). The loops or channels in the respective RF coils in the stages function as a receiver of resonance frequency emitted by molecules in the patient body. As depicted, the stage 184 may be disposed about or wrapped around the upper arm. The stage 186 may be disposed about or wrapped around the forearm. The stage 188 may be disposed about or wrapped around the wrist area. As described in greater detailed below, the positioning of the stages 182 may be adjusted relative to each other to accommodate imaging the arm or a portion of the arm. In certain embodiments, the stages 182 may be adjusted so that at least a couple of the stages 182 overlap with each during the functional imaging. FIG. 2 depicts the stages 182 in a flat state (i.e., without the stages disposed about the extremity). FIG. 3 depicts the stages 182 in a flexed or wrapped state that the stages 182 would be in when disposed about the extremity.

Returning to FIG. 2, each stage 182 (in particular, the circuitry from the RF coil in each stage 182) is coupled to an electrical connector 192. Each electrical connector 192 is coupled to a port cable assembly 194 via a cable 196. The port channel cable assembly is coupled to a P connector 198 (e.g., port connector) that enables the RF multistage receiving coil assembly 180 to be coupled to the interface of the MRI system that couples imaging components to processing components. The signals (e.g., data) from each of the channels within a respective stage 182 are combined and provided to the port cable assembly 194. In certain embodiments, the signals from each of the stages 182 are combined and travel together in the port cable assembly 194. In certain embodiments, the RF multistage receiving coil assembly 180 may include more than one port cable assembly 194 and respective P connector 198. In such an embodiment, one or more stages 182 of the RF multistage receiving coil assembly 180 may be coupled to one port cable assembly 194 and P connector 198, while the other one or more stages 182 may be coupled to another port cable assembly 194 and P connector 198.

In certain embodiments, each stage 182 may be utilized in the functional imaging of the arm. In certain embodiments, only some of the stages 182 may be utilized in the functional imaging of the arm or a portion of the arm. In certain embodiments, only a single stage 182 may be utilized in the functional imaging of a portion of an arm (e.g., upper arm, forearm, wrist, etc.). Thus, the RF multistage receiving coil assembly 180 is configured to operate in a first mode with only some of the stages 182 (e.g., RF coils) selectively activated during a MRI scan and in a second mode with all of the stages 182 (e.g., RF coils) activated during the MRI scan. In certain embodiments, a respective stage 182 may be not be utilized by physically disconnecting the stage 182 from the port cable assembly 194 by disconnecting the electrical connector 192 from the stage 182. In certain embodiments, a respective stage 182 may not be utilized by electrically disconnecting the stage 182 (i.e., turning the power off to the stage 182).

Figure 4:
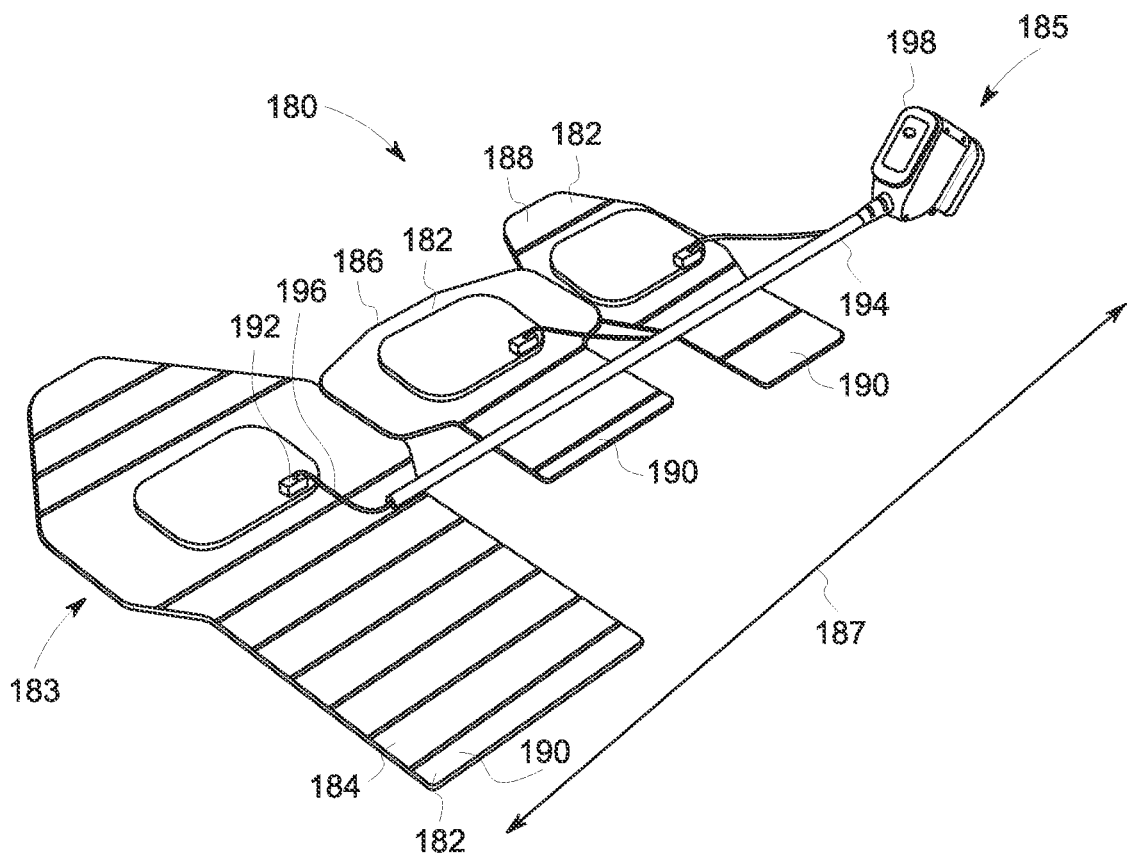
FIG. 4 is a perspective view of an RF multistage receiving coil assembly for functional imaging of an extremity (e.g., with stages in a flat position and having different stage shapes), in accordance with aspects of the present disclosure.
Figure 5:
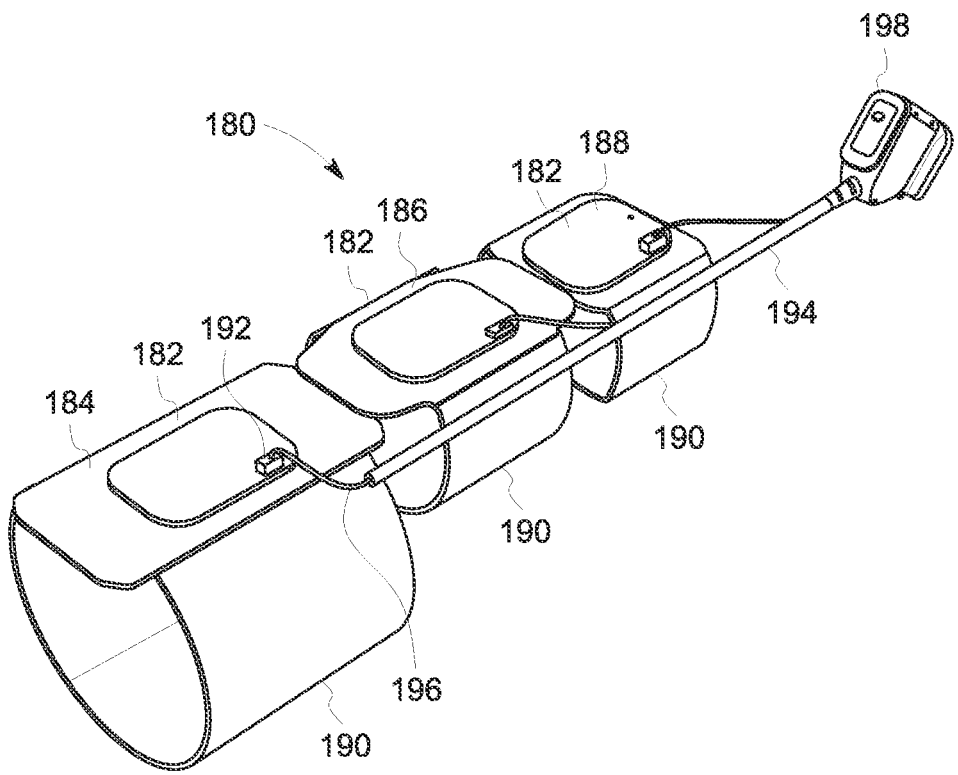
FIG. 5 is a perspective view of an RF multistage receiving coil assembly for functional imaging of an extremity (e.g., with stages in a flat position and having different stage shapes), in accordance with aspects of the present disclosure.

As mentioned above, the shapes and sizes of the stages 182 of the RF multistage receiving coil assembly 180 may vary. In FIGS. 4 and 5, the shapes and sizes of the stages 182 vary from the stages 82 in FIGS. 2 and 3. For example, portions of the stages 182 in FIGS. 4 and 5 narrow in a direction crosswise to the longitudinal length 187. In general, the RF multistage receiving coil assembly 180 is as described in FIGS. 2 and 3.

Figure 6:
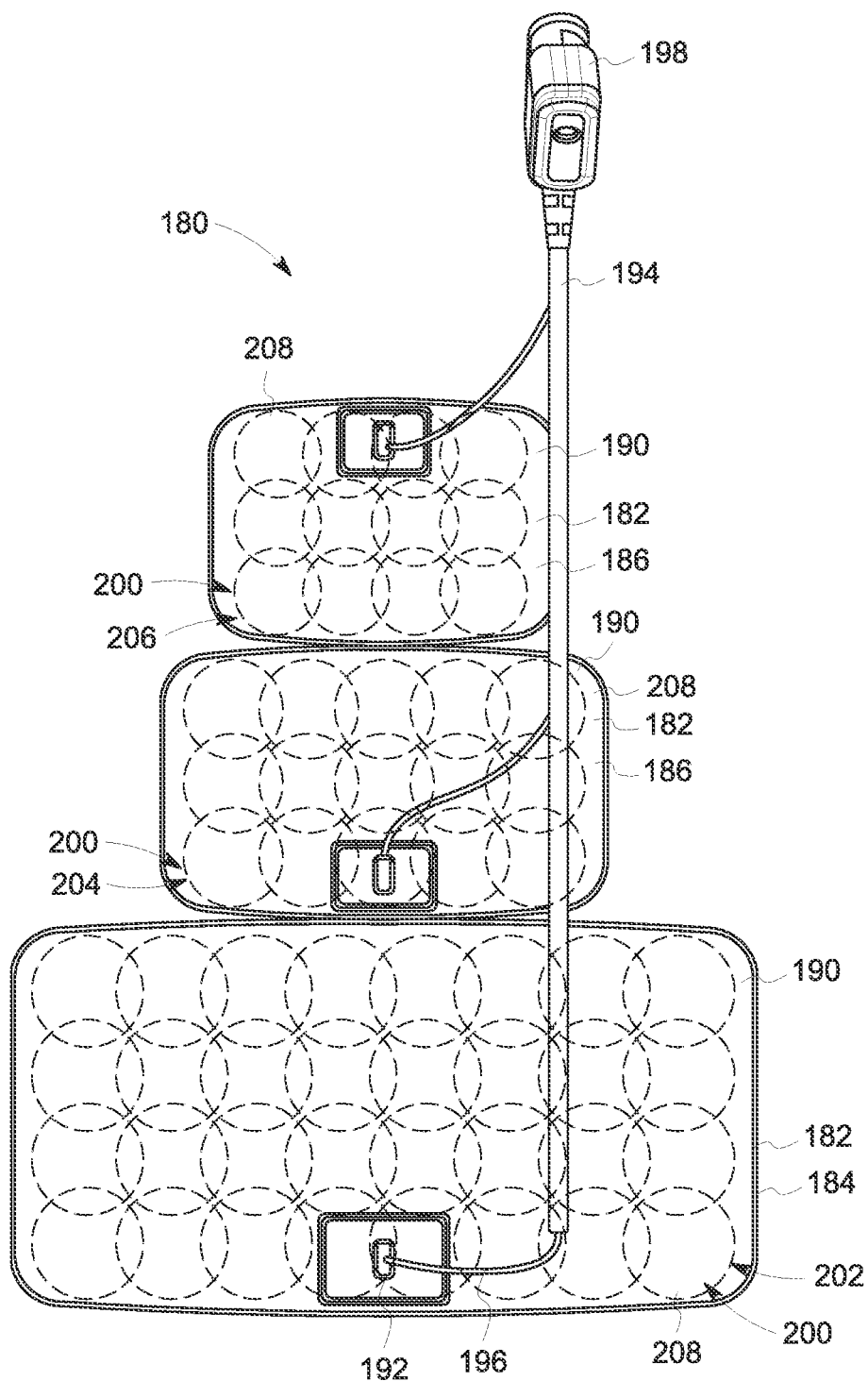
FIG. 6 is a top view of the RF multistage receiving coil assembly in FIGS. 2 and 3 illustrating its coil topology, in accordance with aspects of the present disclosure.

FIG. 6 is a top view of the RF multistage receiving coil assembly 180 in FIGS. 2 and 3 illustrating its coil topology. Multiple coils 200 (e.g., RF coils) form the multistage coil of the multistage coil assembly 180. Stages 184, 186, and 188 include RF coils 202, 204, and 206, respectively. Each RF coil 200 includes a plurality of flexible loops 208 (e.g., elements or channels). The number of loops or channels 208 may vary within the RF multistage receiving coil assembly 180. The number of loops or channels 208 is at least greater than 32 channels. As depicted, the number of loops or channels is 59 loops or channels. The number of loops 208 in each RF coil 200 may vary. As depicted, the RF coil 202 includes 32 loops 208, the RF coil 204 includes 15 loops 208, and the RF coil 206 includes 12 loops 208. The size and shapes of the loops 208 may vary in each RF coil 200. The size and shapes of the loops 208 may also vary between the different RF coils 200. As depicted, in larger stages 182, the RF coil 200 includes more loops 208. In certain embodiments, a smaller stage 182 may have more loops 208 in the RF coil 200 than a larger stage 182. In certain embodiments, loops 208 within a respective RF coil 200 may overlap.

Although not shown, each loop 208 is coupled to an electronics unit coupled to a coil-interfacing cable. The coil-interfacing cables of each of the loops 184 is coupled to the electrical connector. Each loop 208 may consists of linked resonator elements coupled to a printed circuit board module (e.g., the electronics unit). Each electronics unit may include various components (e.g., a decoupling circuit, an impedance inverter circuit, and a pre-amplifier). The RF coils 200 may be designed utilizing AIR™ coil technology from General Electric Healthcare. This enables the RF coil 182 to be lightweight and flexible. Each loop 208 includes a malleable (e.g., flexible) conductor that enables complex and irregular surface contours. In certain embodiments, each loop 208 may stretch (e.g., due to a liquid metal conductor). Alternatively, each loop 208 may include litz wire, a regular stranded wire, or a spiral wire woven on an extendible non-conductive support or a meandering trace. In addition, the loops 208 of the RF coil 200 are transparent, thus, aiding signal-to-noise ratios. Due to the high channel count and the flexibility of the loops 208, the RF multistage receiving coil assembly 180 maximizes acceleration in all directions during parallel imaging to provide efficient capture of movement and related stress of the muscles of the extremity.

Figure 7:
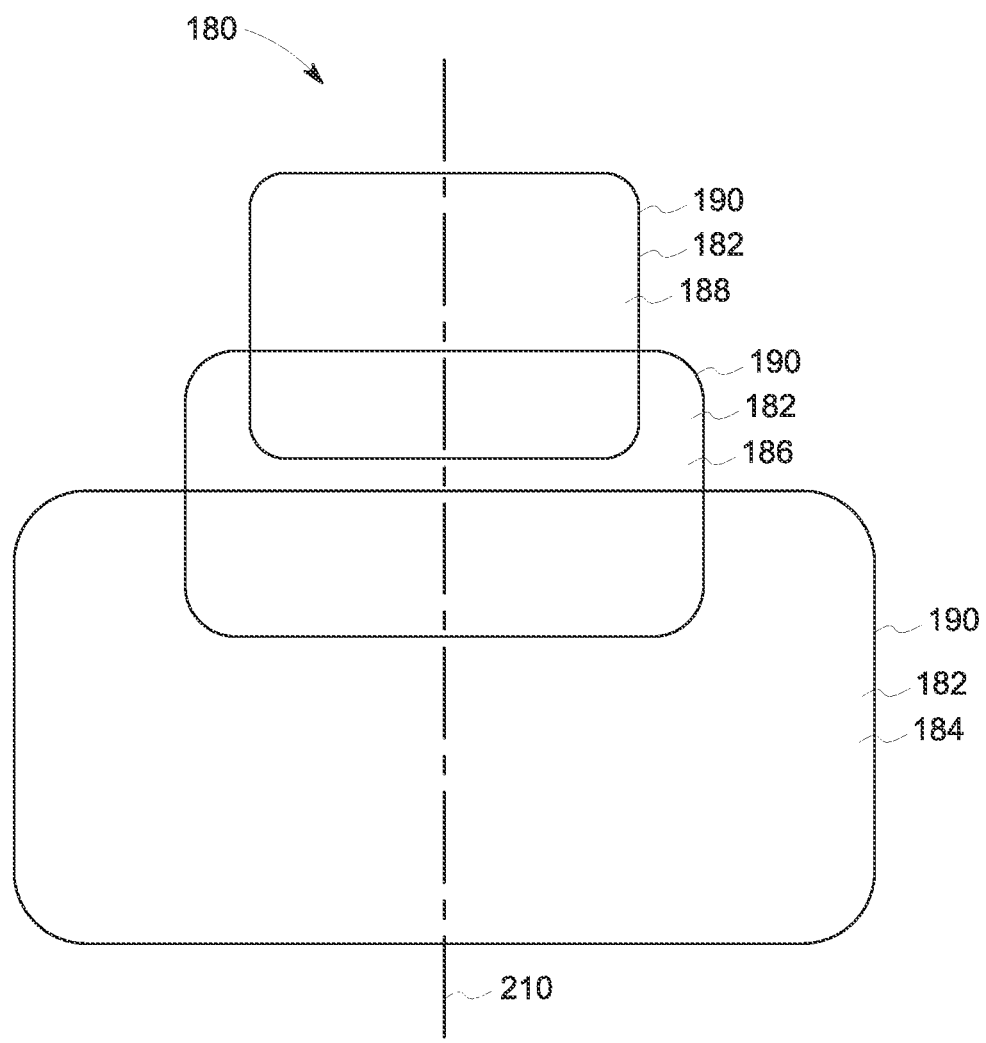
FIG. 7 is a schematic view of the RF multistage receiving coil assembly (e.g., illustrating movement of stages relative to each other), in accordance with aspects of the present disclosure.

As noted above, the stages 182 of the RF multistage receiving coil assembly 180 may be moved relative to each other (i.e., the stages are adjustable). FIG. 7 is a schematic view of the RF multistage receiving coil assembly 180 (e.g., illustrating movement of the stages 182 relative to each other). The components of the RF multistage receiving coil assembly 180 coupling each stage 182 to the port cable assembly are not shown. Each stage 182 of the plurality of stages 182 is configured to be moved with respect to each other along a longitudinal axis 210 of the RF multistage receiving coil assembly 180. As depicted, each stage 182 has been moved along long longitudinal axis 210 so that stage 188 partially overlaps with stage 186 and stage 186 partially overlaps with stage 184. In certain embodiments, only a couple of the stages 182 may at least partially overlap with each other. In certain embodiments, more than two of the stages 182 may at least partially overlap with another stage 182. In certain embodiments, more than two of the stages 182 may at least partially overlap with each other (e.g., stages 184, 186, and 188 would all at least partially overlap). In certain embodiments, one of the stages 182 may completely overlap with another stage 182. In certain embodiments, the stages 182 may be adjusted or moved along the longitudinal axis 210 to further move the stages 182 apart from each other.

Figure 8:
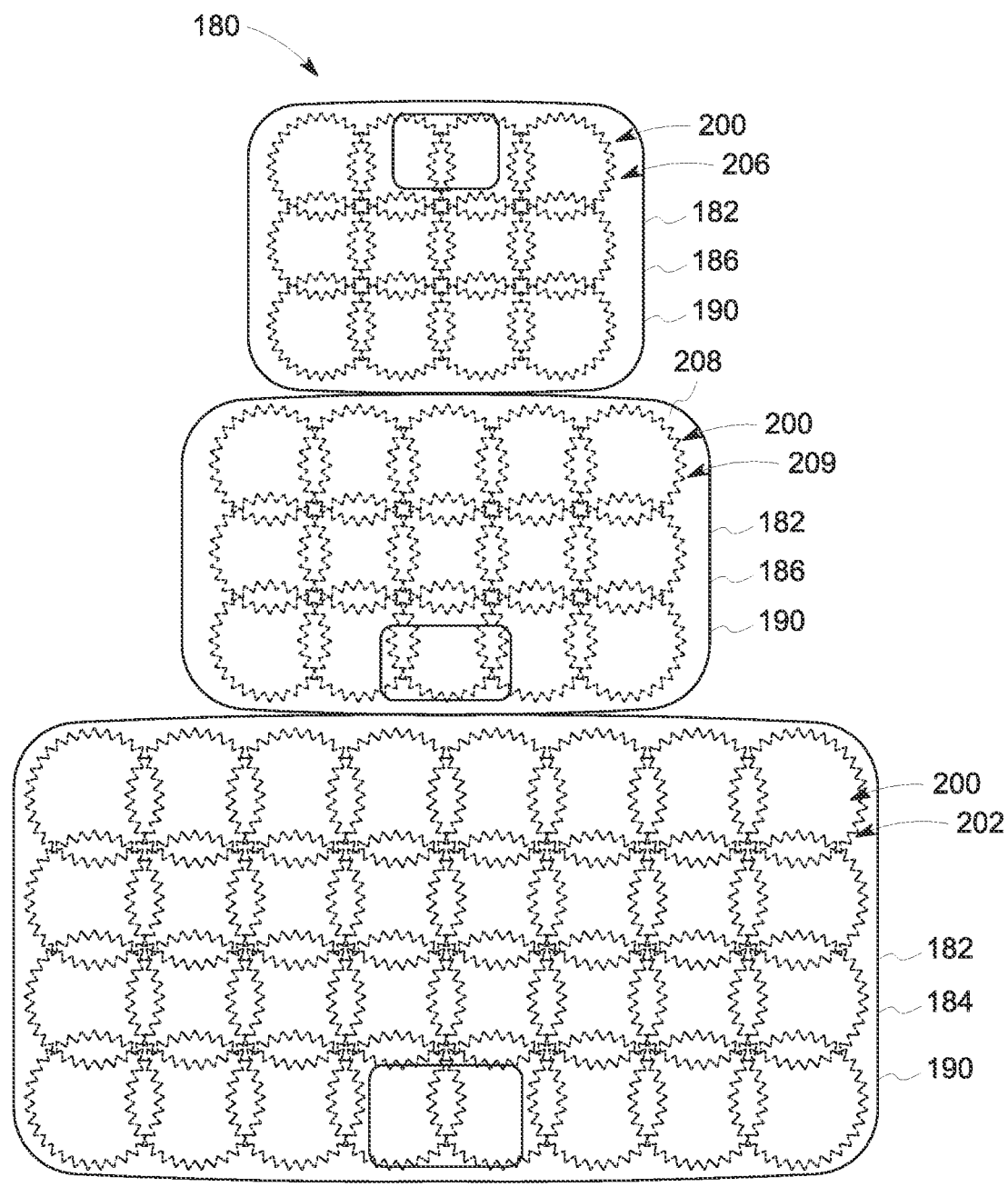
FIG. 8 is a top view of a RF multistage receiving coil assembly having stretchable loops (e.g., in a relaxed state), in accordance with aspects of the present disclosure.
Figure 9:
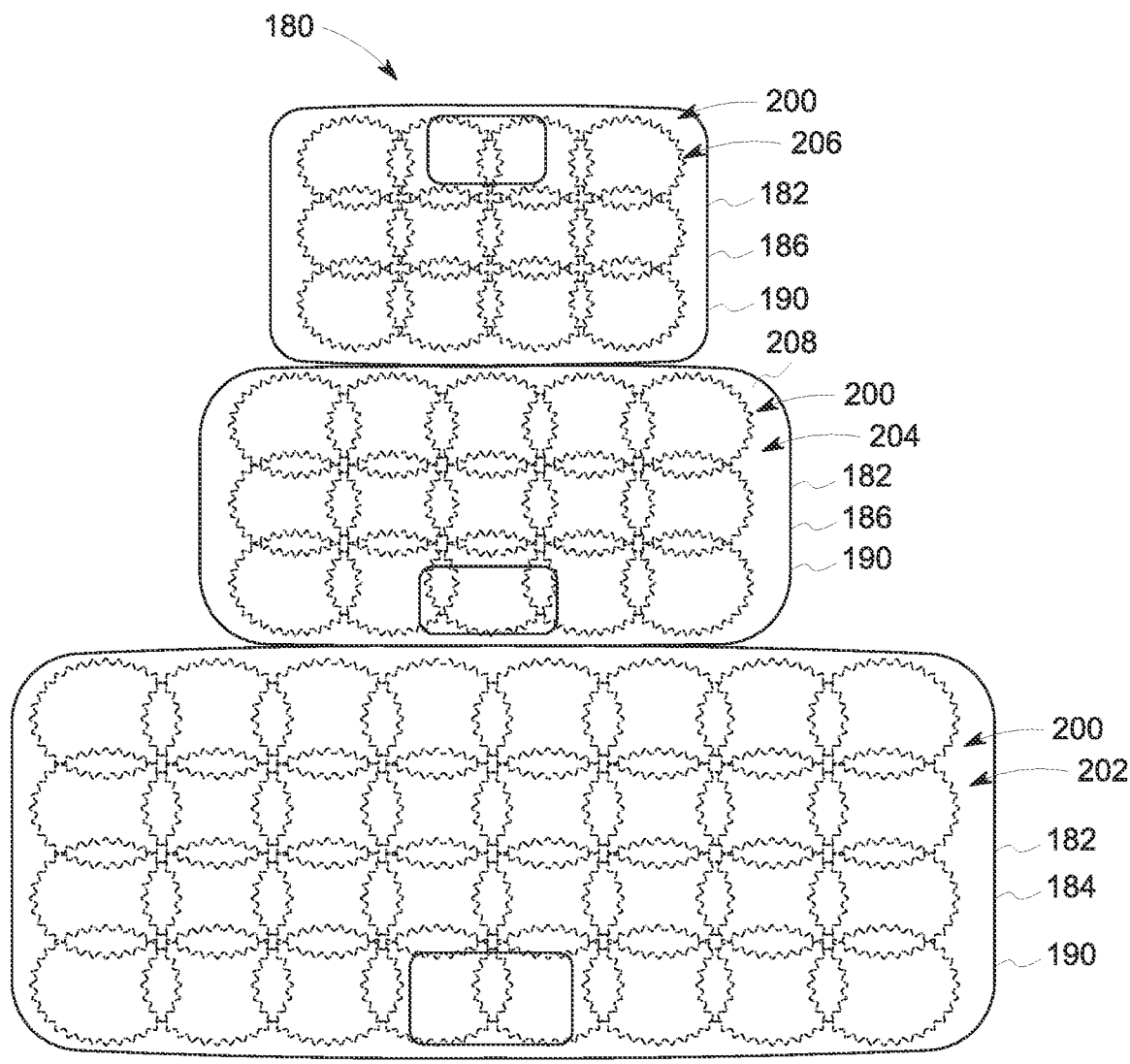
FIG. 9 is a top view of the RF multistage receiving coil assembly having stretchable loops in FIG. 8 (e.g., in a stretched state), in accordance with aspects of the present disclosure.
Figure 10:
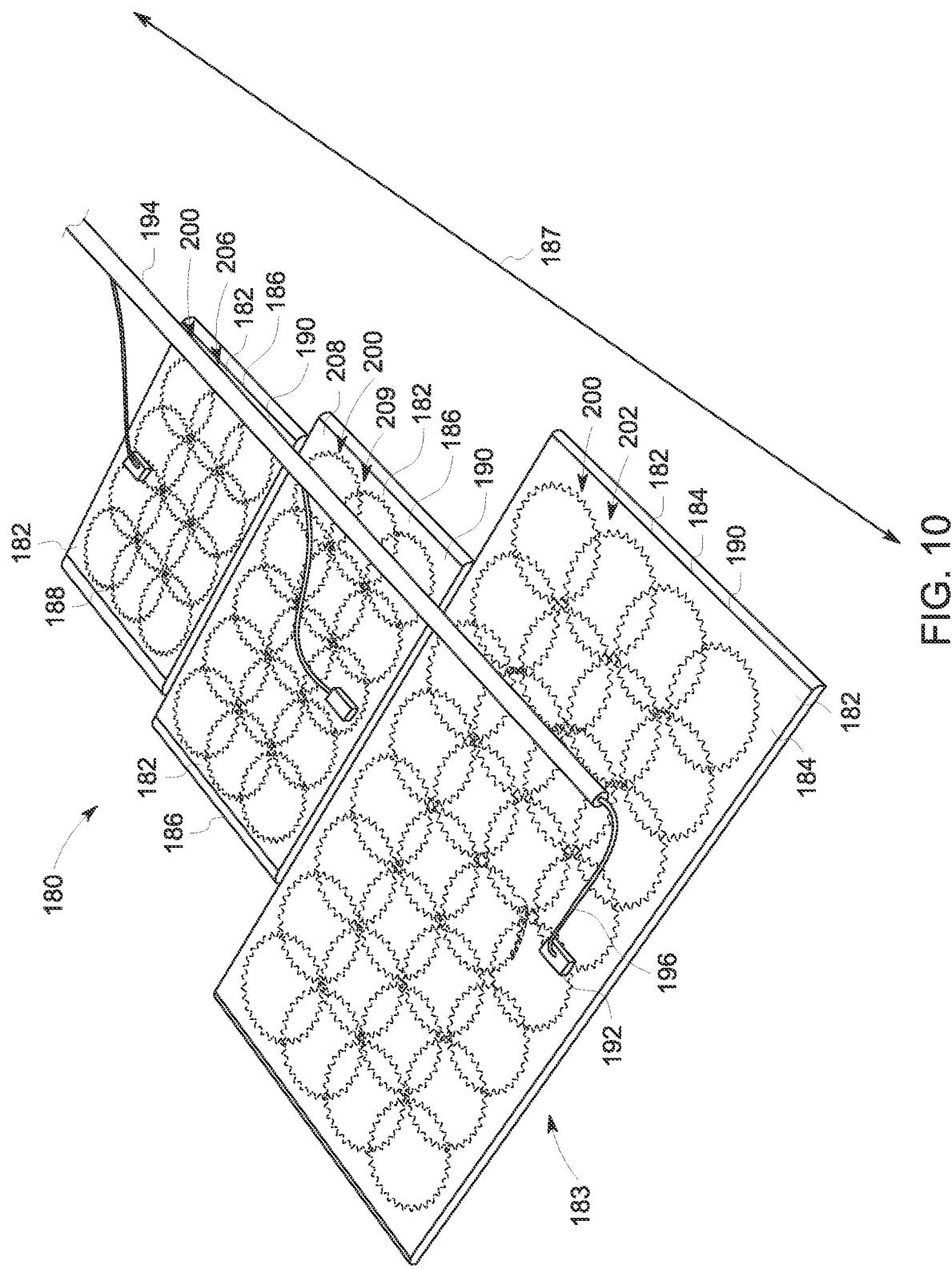
FIG. 10 is a perspective view of an RF multistage receiving coil assembly having stretchable loops (e.g., with stages in a flat position and loops in a relaxed state), in accordance with aspects of the present disclosure.
Figure 11:
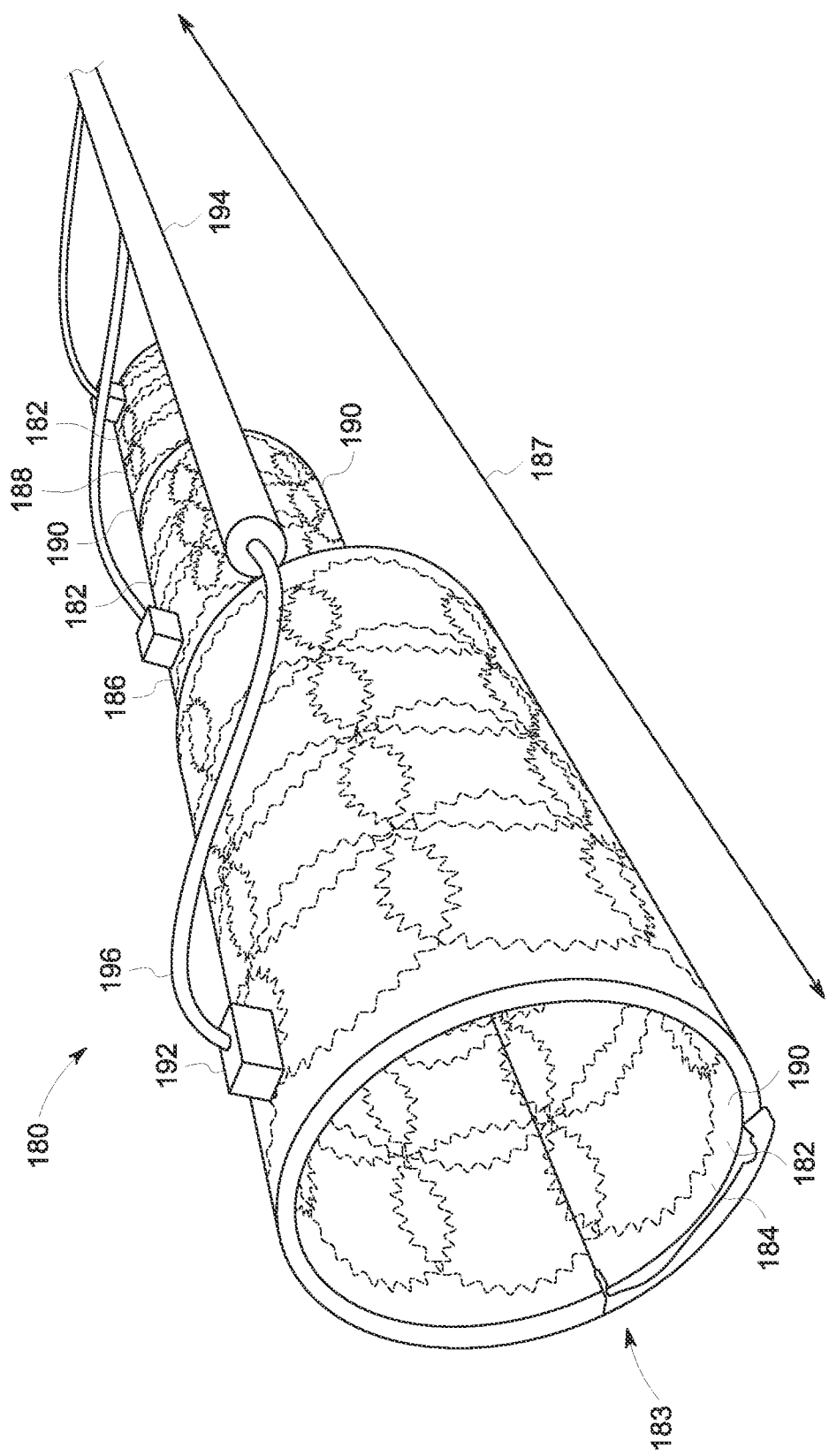
FIG. 11 is a perspective view (e.g., from the upper arm end) of an RF multistage receiving coil assembly in FIG. 10 (e.g., with stages in a flexed position and loops in a relaxed state), in accordance with aspects of the present disclosure.
Figure 12:
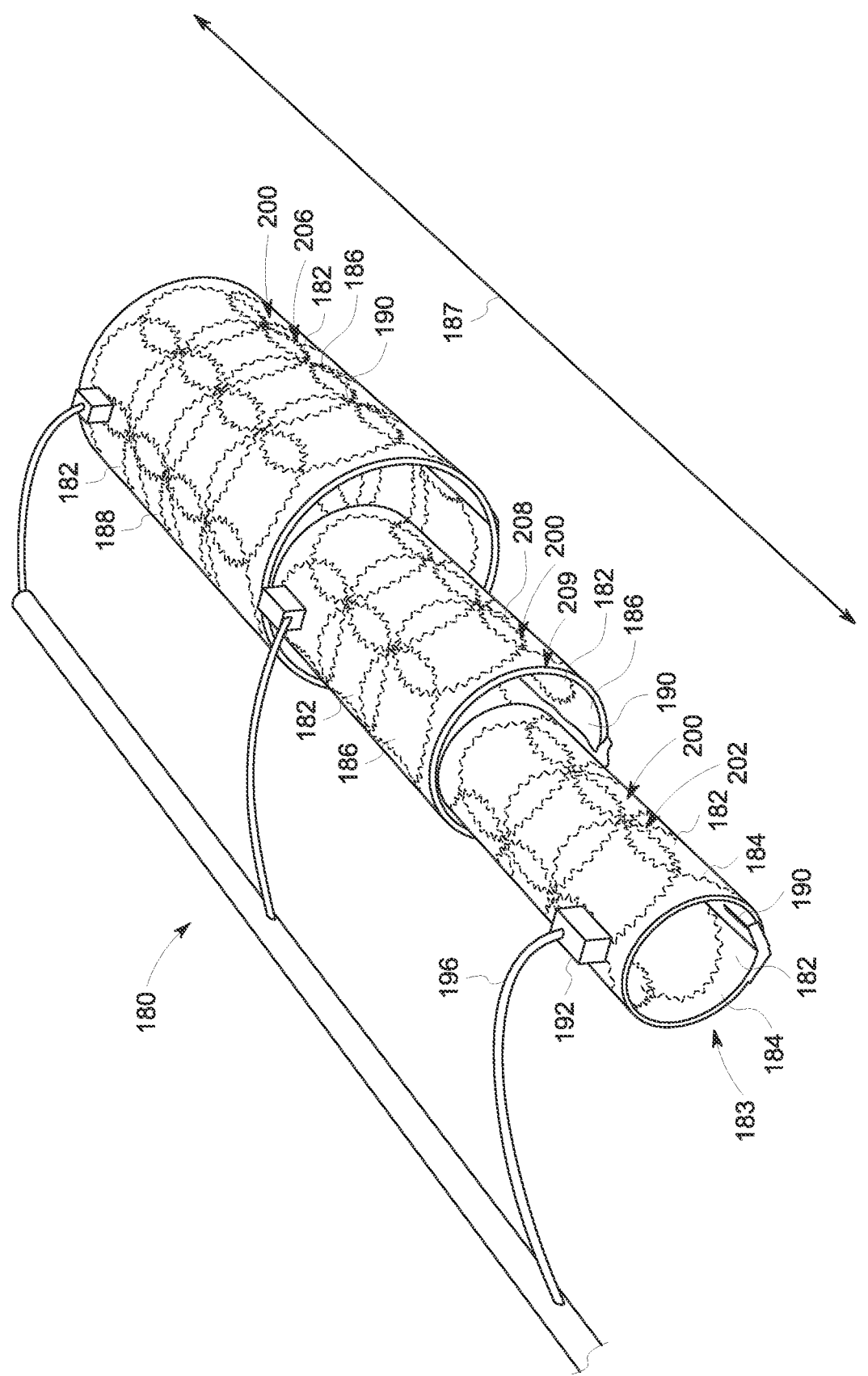
FIG. 12 is a perspective view (e.g., from the wrist end) of an RF multistage receiving coil assembly in FIG. 10 (e.g., with stages in a flexed position and loops in a relaxed state), in accordance with aspects of the present disclosure.
Figure 13:
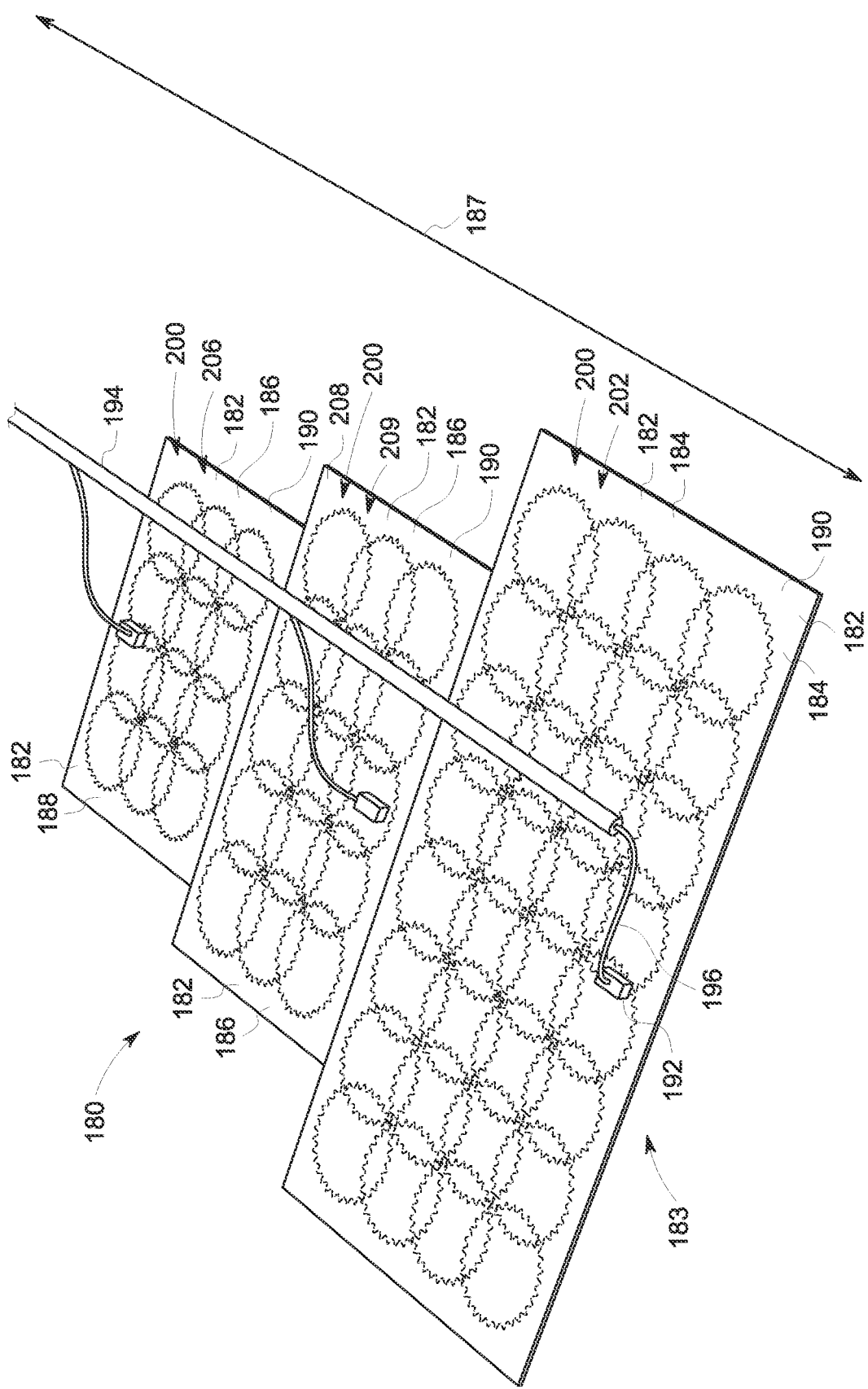
FIG. 13 is a perspective view of an RF multistage receiving coil assembly having stretchable loops (e.g., with stages in a flat position and loops in a stretched state), in accordance with aspects of the present disclosure.
Figure 14:
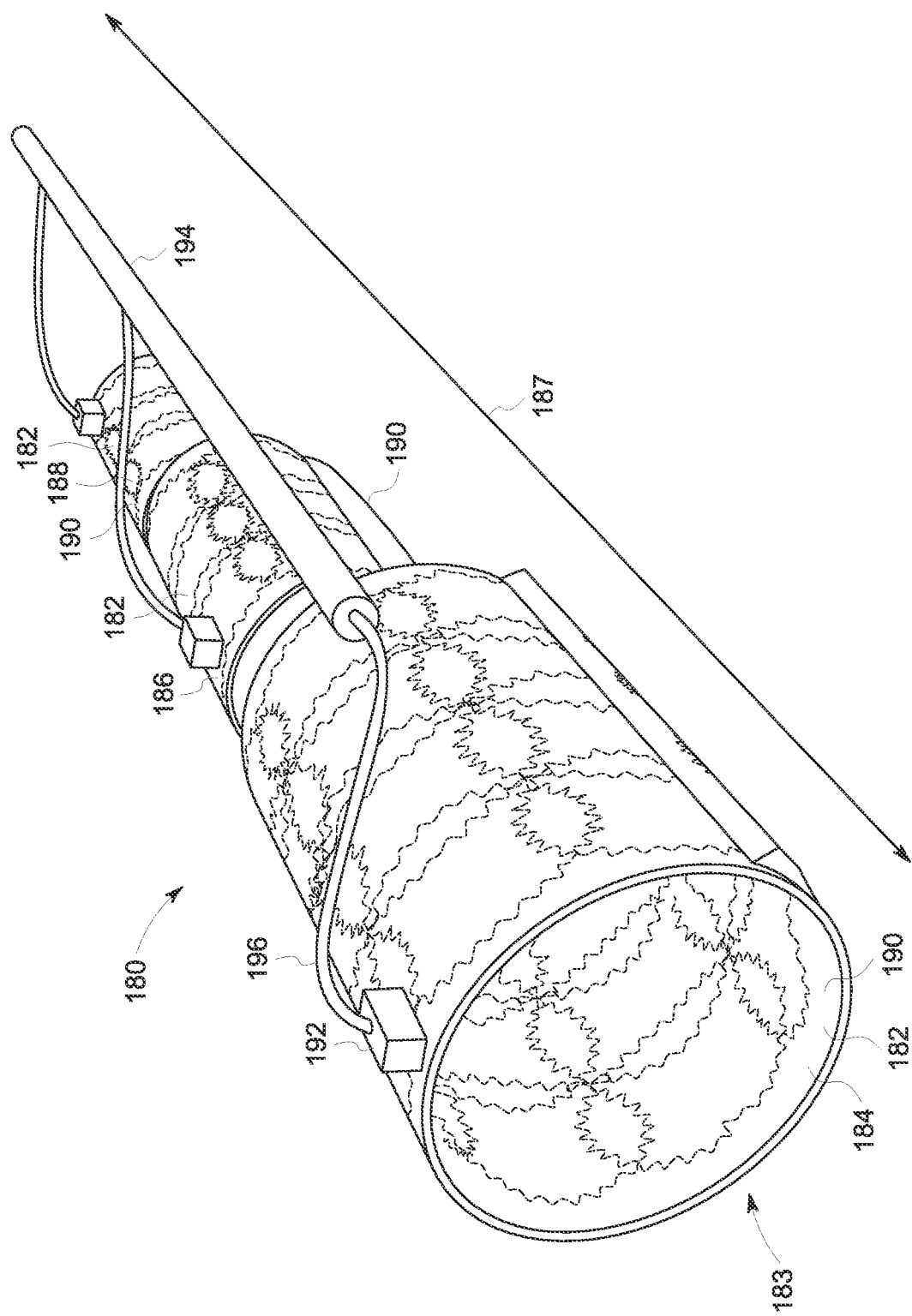
FIG. 14 is a perspective view (e.g., from the upper arm end) of an RF multistage receiving coil assembly in FIG. 13 (e.g., with stages in a flexed position and loops in a stretched state), in accordance with aspects of the present disclosure.
Figure 15:
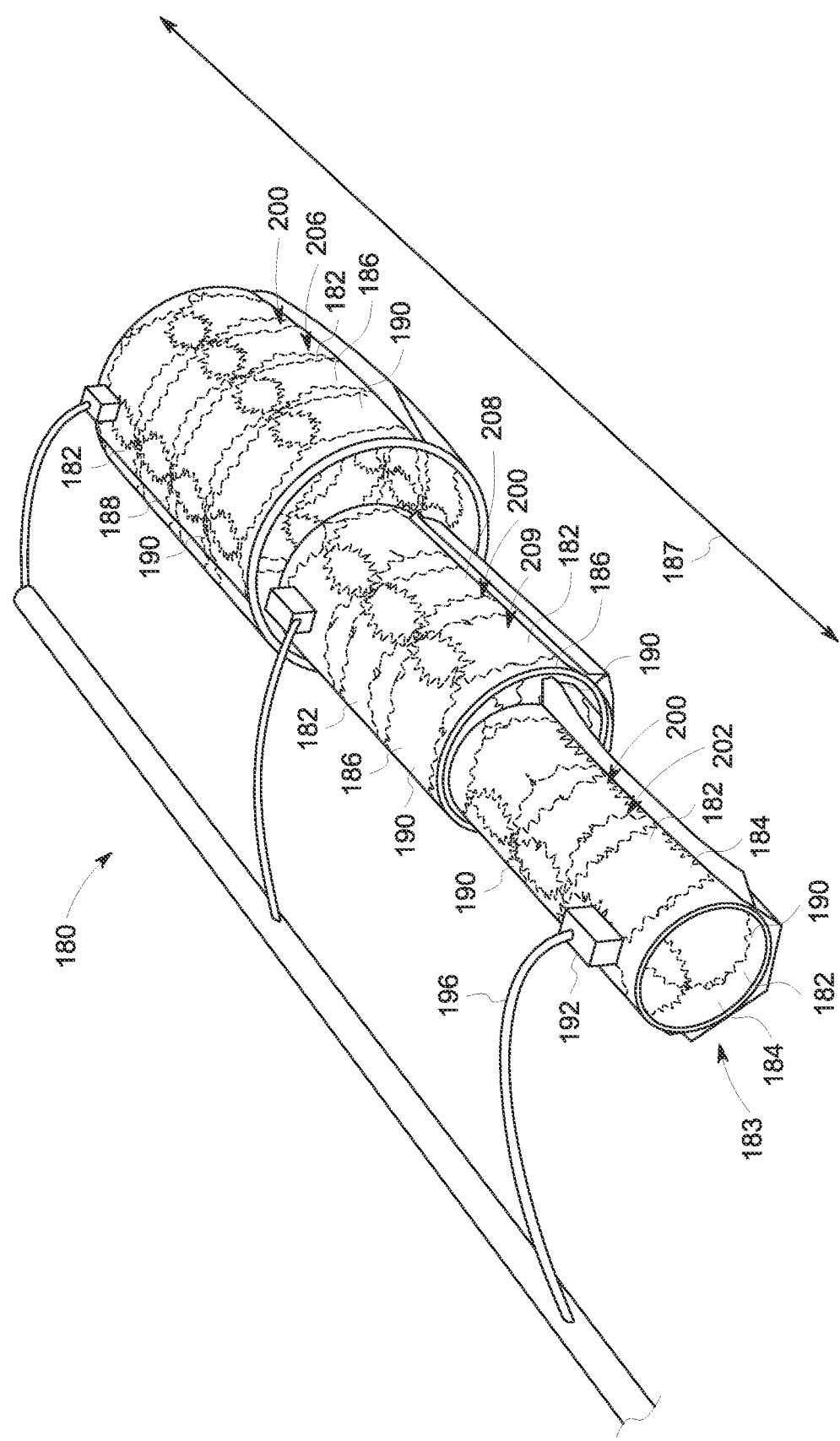
FIG. 15 is a perspective view (e.g., from the wrist end) of an RF multistage receiving coil assembly in FIG. 13 (e.g., with stages in a flexed position and loops in a stretched state), in accordance with aspects of the present disclosure.

As noted above, the loops 208 of the RF coils 200 of the RF multistage receiving coil assembly 180 may be stretchable. FIG. 8 is a top view of the RF multistage receiving coil assembly 180 having stretchable loops 208. The components of the RF multistage receiving coil assembly 180 coupling each stage 182 to the port cable assembly are not shown. In general, the RF multistage receiving coil assembly 180 is as described above (e.g., in FIGS. 2 and 3). The RF loops 208 are configured to stretch (e.g., due to having a liquid metal conductor or a meandering trace). This enables the RF loops 208 of the RF coils to better conform about the extremity to be imaged. Each loop 208 is arranged with a zig-zag pattern along an outline of a circular or elliptical shape of the loop 184. The angles along the zig-zag pattern are rounded. The design for the coils configured to stretch can be utilized in any topology for the RF coil 200 where it is desirable for a portion of the RF coil 200 to be stretched. In certain embodiments, all or only some of the RF coils 200 may include stretchable loops 208. As depicted in FIG. 8, the stretchable loops 208 are in a relaxed stated. In FIG. 9, the stretchable loops 208 are in a stretched state. It should be noted that the flexible enclosures 190 are also in a relaxed and stretched state, respectively, in FIGS. 8 and 9. FIGS. 10-15 illustrate perspective views of an entire RF multistage receiving coil assembly 180 having stretchable loops 208. FIGS. 10-12 illustrate the loops 208 in a relaxed state. FIGS. 13-15 illustrate the loops 208 in a stretched state. FIGS. 10 and 13 illustrate the stages 182 in a flat position. FIGS. 11, 12, 14, and 15 illustrate the stages 182 in a flexed position (e.g., when disposed around an extremity).

Figure 16:
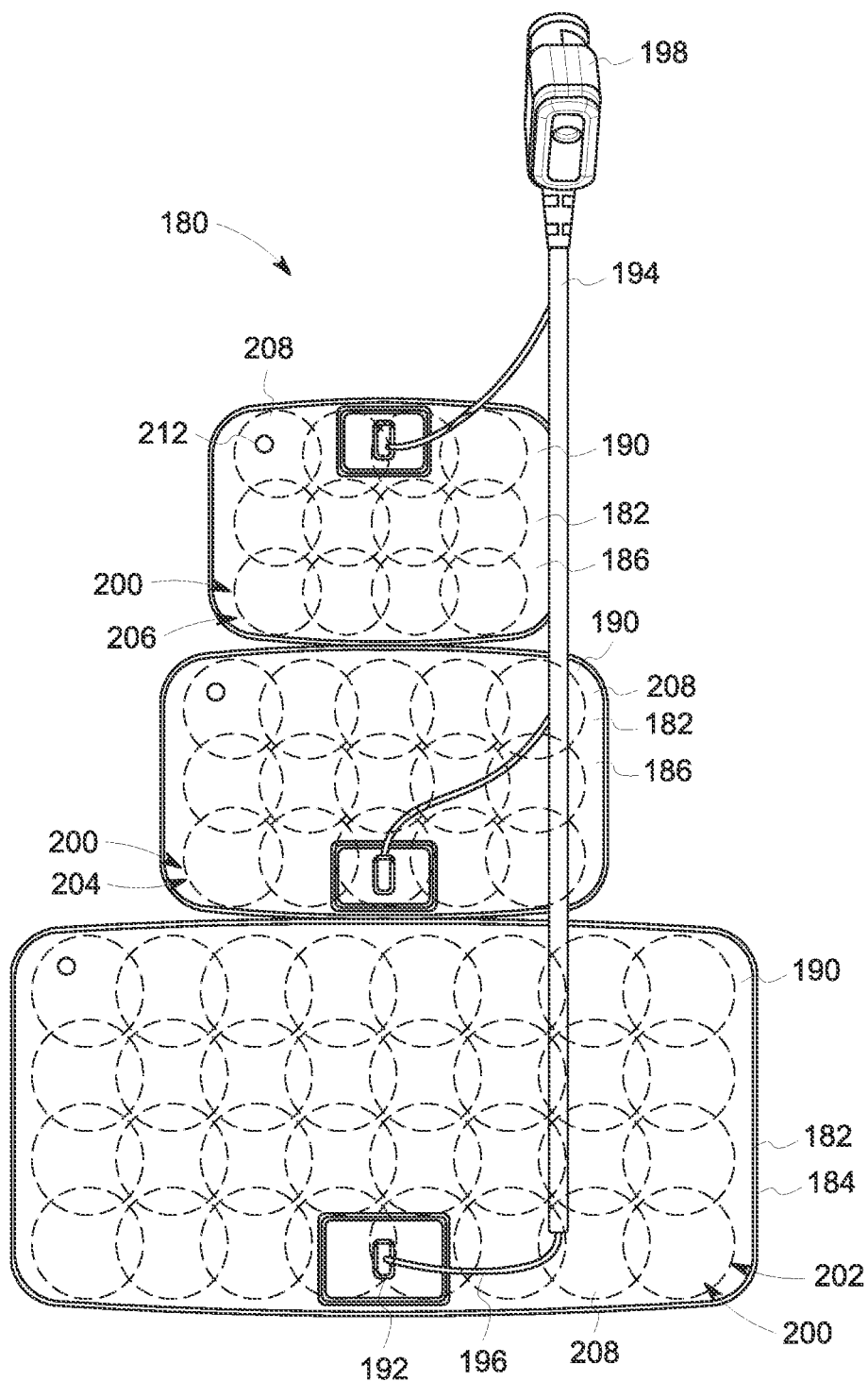
FIG. 16 is a top view of the RF multistage receiving coil assembly in FIG. 6 having holes in the flexible enclosures, in accordance with aspects of the present disclosure.

FIG. 16 is a top view of the RF multistage receiving coil assembly 180 in FIG. 6 having holes or openings 212 in the flexible enclosures 190. Each hole or opening 212 may be radially located within the loop 208 (i.e., located within a respective perimeter of a loop). The openings 224 increases the flexibility of the stages 182 and enables them to be stretched about the extremity. In certain embodiments, the flexible enclosure 191 may include deformable material within. As depicted, the holes 212 are disposed within each loop 208. In certain embodiments, the holes 212 may only be disposed within some of the loops 208. As depicted, each stage 182 includes holes 212 within the loops 208. In certain embodiments, the holes 212 may be utilized on only some of the stages 182. In certain embodiments, the holes 212 may be utilized in conjunction with stretchable loops 208 as described in FIGS. 8-15.

Technical effects of the disclosed embodiments include providing an RF multistage receiving coil assembly that enables functional imaging (e.g., of functional attributes) of an extremity (e.g., arm or leg). The RF multistage receiving coil assembly includes multiple stages or segments, wherein each segment includes an RF receiving coil disposed within a flexible enclosure. Each RF receiving coil includes multiple flexible loops (e.g., elements or channels) having a malleable conductor. Due to the high channel count and the flexibility of the loops, the RF multistage receiving coil assembly maximizes acceleration in all directions during parallel imaging to provide efficient capture of movement and related stress of the muscles of the extremity.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A radio frequency (RF) multistage receiving coil assembly for a magnetic resonance imaging (MRI) system, comprising:
   a plurality of RF coils, wherein each RF coil of the plurality of RF coils comprises a plurality of flexible loops having a malleable conductor; and
   a plurality of flexible enclosures, wherein each respective RF coil of the plurality of RF coils is separately disposed within a different flexible enclosure of the plurality of flexible enclosures;
   wherein each respective RF coil disposed within a respective different flexible enclosure forms a respective stage, and the RF multistage receiving coil assembly comprises a plurality of stages, wherein each stage of the plurality of stages of the RF multistage receiving coil assembly is configured to be adjusted and disposed about an extremity of a subject to enable functional imaging of the extremity with the MRI system, and wherein each stage of the plurality of stages is configured to be individually moved with respect to each other both along a longitudinal axis of the RF multistage receiving coil assembly and along a length of the extremity when the plurality of stages are disposed about the extremity.

2. The RF multistage receiving coil assembly of claim 1, wherein each flexible loop of the plurality of loops is configured to stretch when the RF multistage receiving coil assembly is disposed about the extremity.

3. The RF multistage receiving coil assembly of claim 1, wherein at least one flexible enclosure of the plurality of flexible enclosures comprises a hole located within a respective perimeter of one or more flexible loops of the plurality of flexible loops, wherein the hole is configured to enable the at least one flexible enclosure to stretch.

4. The RF multistage receiving coil assembly of claim 1, wherein the RF multistage receiving coil assembly is configured to operate with only some of the plurality of RF coils selectively activated.

5. The RF multistage receiving coil assembly of claim 1, wherein the RF multistage receiving coil assembly comprises 3 stages.

6. The RF multistage receiving coil assembly of claim 1, wherein at least one stage is configured to overlap with one or more other stages when disposed about the extremity during a functional imaging scan so that at least a portion of the one or more stages is concentrically disposed within the at least one stage.

7. The RF multistage receiving coil assembly of claim 1, wherein the RF multistage receiving coil assembly is configured to be utilized during an accelerated scan.

8. The RF multistage receiving coil assembly of claim 1, wherein the RF multistage receiving coil assembly comprises greater than 32 flexible loops.

9. The RF multistage receiving coil assembly of claim 1, wherein at least one RF coil of the plurality of RF coils has a different number of flexible loops from one or more of the other RF coils.

10. A magnetic resonance imaging (MRI) system, comprising:
an imaging portion having a radio frequency (RF) multistage receiving coil assembly, wherein the RF multistage receiving coil assembly comprises:
a plurality of RF coils, wherein each RF coil of the plurality of RF coils comprises a plurality of flexible loops having a malleable conductor; and
a plurality of flexible enclosures, wherein each respective RF coil of the plurality of RF coils is separately disposed within a different flexible enclosure of the plurality of flexible enclosures;
wherein each respective RF coil disposed within a respective different flexible enclosure forms a respective stage, and the RF multistage receiving coil assembly comprises a plurality of stages, wherein each stage of the plurality of stages of the RF multistage receiving coil assembly is configured to be adjusted and disposed about an extremity of a subject to enable functional imaging of the extremity with the MRI system, and wherein each stage of the plurality of stages is configured to be individually moved with respect to each other both along a longitudinal axis of the RF multistage receiving coil assembly and along a length of the extremity when the plurality of stages are disposed about the extremity.

11. The MRI system of claim 10, wherein each flexible loop of the plurality of loops is configured to stretch when the RF multistage receiving coil assembly is disposed about the extremity.

12. The MRI system of claim 10, wherein at least one flexible enclosure of the plurality of flexible enclosures comprises a hole located within a respective perimeter of one or more flexible loops of the plurality of flexible loops, wherein the hole is configured to enable the at least one flexible enclosure to stretch.

13. The MRI system of claim 10, wherein the RF multistage receiving coil assembly is configured to operate with only some of the plurality of RF coils selectively activated.

14. The MRI system of claim 10, wherein the RF multistage receiving coil assembly is configured to be utilized during an accelerated scan.

15. The MRI system of claim 10, wherein the RF multistage receiving coil assembly comprises greater than 32 flexible loops.

16. The MRI system of claim 10, wherein at least one RF coil of the plurality of RF coils has a different number of flexible loops from one or more of the other RF coils.

17. The RF multistage receiving coil assembly of claim 1, wherein each stage of the plurality of stages has a different size from other stages of the plurality of stages.

* * * * *